United States Patent [19]
Peters

[11] Patent Number: 5,834,505
[45] Date of Patent: Nov. 10, 1998

[54] ANTIMALARIAL DRUGS

[75] Inventor: Wallace Peters, Berkhamsted, United Kingdom

[73] Assignee: Pharma Mar, S.A., Madrid, Spain

[21] Appl. No.: 752,454

[22] Filed: Nov. 15, 1996

[30] Foreign Application Priority Data

Oct. 28, 1996 [GB] United Kingdom .................. 9622427

[51] Int. Cl.$^6$ .......................... A61K 31/36; A61K 31/44
[52] U.S. Cl. ............................................. 514/454; 514/299
[58] Field of Search ..................................... 514/454, 299

[56] References Cited

FOREIGN PATENT DOCUMENTS 0 286 316 A1  3/1988  European Pat. Off. .

OTHER PUBLICATIONS

Microbiological Reviews, Jun. 1996, "Artemisinin and the Antimalarial Endoperoxides: from Herbal Remedy to Targeted Chemotherapy", vol. 60, No. 2, pp. 301–315.

W. Peters, et al., *Annals of Tropical Medicine and Parasitology*, 1970, vol. 64, pp. 41–51.

W. Peters, et al., *Annals of Tropical Medicine and Parasitology*, vol. 87, pp. 9–16 (1993).

Charles W. Jefford, *J. Chem. Soc., Chem. Commun.*, 1984, pp. 523–524.

W. Clark Still, et al., *J. Am. Chem. Soc.*, 1983, vol. 105, pp. 625–627.

Charles W. Jefford, *J. Am. Chem. Soc.*, 1983, vol. 105 pp. 6497–6498.

Jefford, et al., *Chemical Abstract*, 1987, vol. 106, No. 15, pp. 645, col. 1, abstract no. 119857g.

*Helvetica Chimica Acta*, vol. 69, 1986, pp. 941–948.

*Primary Examiner*—Zohreh Fay
*Attorney, Agent, or Firm*—Ernest V. Linek; Dike, Bronstein, Roberts & Cushman, LLP

[57] ABSTRACT

An antimalarial drug combination for prophylactic treatment or curative treatment of malaria comprises a first component which is a fenozan, that is a cis-fused cyclopenteno-1,2,4-trioxane, and a second component which is another antimalarial drug.

7 Claims, 4 Drawing Sheets

ANTIMALARIAL DRUGS

BACKGROUND OF THE INVENTION

Malaria is caused by protozoan parasites, notably *Plasmodium falciparum*. The range of drugs available on the market for prevention and treatment of malaria is limited, and there are problems of drug resistance.

EP-A 286,316 describes 1,2,4-trioxane derivatives with antimalarial activity. Structure activity studies led to the identification of cis-(±)4a,7a-dihydro-6,7a-di(p-fluorophenyl)spiro(cylopentane-3,3'-7-cyclopenta-1,2,4-trioxane) as the most potent compound, see Annals of Tropical Medicine and Parasitology, 87, 9 to 16 (1993). This particular compound, referred to as fenozan-50F and now known as fenozan B07, has the structure shown in FIG. 1 of the accompanying drawings.

Data for this compound, both in vitro and in vivo, was presented at the 44th Annual Meeting of the American Society of Tropical Medicine and Hygiene in San Antonio, Tex. in November 1995 The data suggested there was no cross-resistance with other standard anti-malarial drugs, and it was concluded that B07 has potent activity, with farther studies on resistance mechanism and drug combinations in hand. It was further reported that the compound is being assessed for clinical development.

OBJECT OF THE INVENTION

The object of the present invention is to provide combination drugs of the 1,2,4-trioxanes with enhanced activity.

SUMMARY OF THE INVENTION

The present invention provides a combination antimalarial drug treatment for prophylactic treatment or curative treatment of malaria. One component employed in the combination treatment is a fenozan, that is a cis-fused cyclopenteno-1,2,4-trioxane.

PREFERRED EMBODIMENTS

The cis-fused cyclopenteno-1,2,4-trioxane is preferably such a compound within claim 1 of EP-A 286,316. More preferably the cis-fused cyclopenteno-1,2,4trioxane is a cis-4a,7a-dihydro-7H-cyclopenta-1,2,4-trioxane, most preferably a cis-4a,7a- dihydro-spiro(cyclopentane-3,3'-7H-cyclopenta-1,2,4-trioxane) such as fenozan B07 or one of its close congeners.

The cis-fused cyclopenteno-1,2,4-trioxane component is used in combination by simultaneous or serial administration with another antimalarial drug forming the second component of the combination drag treatment. Suitable candidate drugs for use as the second component include antimalarial arylaminoalcohols, 4-aminoquinolines, folate-synthesis inhibitors, 8-aminoquinolines, antibiotics, peroxides (sesquiterpene lactones), naphthoquinones and iron-chelating agents. We exclude the use of pyronaridine as the second component, in view of a negative test result.

The combination is preferably a synergistic combination, where the activity of the combination is greater than that of the individual components. To this end the second component is preferably chosen from artemisinin, sodium artesunate, chloroquine or mefloquine.

For simultaneous administration, the present invention provides a pharmaceutical composition containing the first and second components, together with a pharmaceutically acceptable carrier. The pharmaceutical composition is preferably formulated for oral administration, and may take the form of a solid or a liquid. Suitable solid formulations include tablets, and suitable liquid formulations include oil-in-water emulsions.

The present invention also provides a method of antimalarial treatment using the first and second components by simultaneous or serial administration.

The present invention further provides the use of the first and second components in the preparation of an antimalarial medicament for use in combination treatment by simultaneous or serial administration.

The amounts of the first and second components are widely variable, and may be readily determined by experiment.

EXAMPLES

Figure 1:
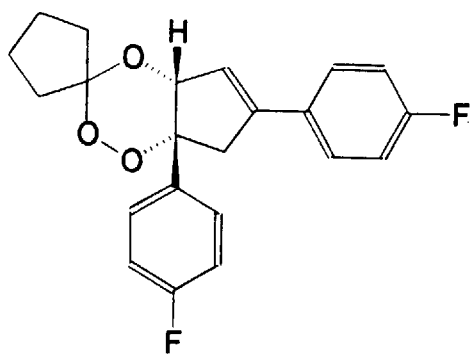
FIG. 1 shows the chemical structure of fenozan B07.

The following pages give the experimental protocol and data for FIGS. 2 to 8 to illustrate the interaction for combination drugs containing the cis-fused cyclopenteno-1,2,4trioxane B07 in combination with known antimalarial drugs.

Experimental Protocol

Animal Accommodation

The Animal Unit consists of a suite of four specially designed rooms within a closed unit. The Unit is held at a temperature of 20°±2° C. and 55% Relative Humidity (±10%) with a dedicated air conditioning system. The rooms are kept under positive pressure with an exchange flow of 320 cubic feet/minute, providing 20 air changes each hour. The animals are housed in groups of five in North Kent Plastic RM2 cages (32×20×20 cm.) and are maintained on a diet of SDS RM3 Expanded Diet and water ad libitum.

Procedures

Blood Schizontocidal Activity

The initial evaluation of blood schizontocidal activity is carried out using the "4 day suppressive test" [See Ann. Trop. Med. Parasit., 64;41–51 (1970)]. A battery of strains of rodent malaria, comprised of a range of drug-sensitive and drug-resistant lines of *Plasmodium berghei* and *P. yoelii*, is maintained for this purpose. The compounds are tested initially against drug-sensitive *P. berghei* N and *P. y. nigeriensis* NIG strain together with chloroquine-resistant *P. yoelii* sp NS strain. These strains of *P. yoelii* have been incorporated into the preliminary screen because they have been found to be a far better model for *P. falciparum* than *P. berghei*. *P. berghei* N strain is also included since most of the lines resistant to standard antimalarials, which have been developed over the years, have this as their parent strain. Compounds which show activity in these preliminary tests are further tested against a range of resistant lines and tested for curative action.

Hosts and Parasites

Vertebrate Host.

Random bred Swiss albino mice (TFW strain, supplied by A. Tuck and Son, Rayleigh, Essex) free of *Eperythrozoon coccoides* weighing between 18 and 20 grams are used for all of the tests. It is important that mice are free of *E. coccoides* and if there is any evidence of these organisms being present, treatment with either neoarsphenamine benzoate or tetracycline is commenced immediately.

Parasite Species and Strains.

*P. berghei* i. N(=Keyberg 173): Sensitive to all standard antimalarial drugs. Does not product gametocytes Maintained by syringe passage.

ii. ANKA: Sensitive to all standard antimalarials. Maintained by cyclical passage through *A. stephensi*.

iii. P—derived from N: Highly resistant to primaquine. Maintained by syringe passage under primaquine pressure (60 mg/kg/day s.c.).

iv. B—derived from N: Highly resistant to cycloguanil. Maintained by syringe passage under cycloguanil pressure (60 mg/kg/day s.c.).

v. PYR—derived from NK 65: Highly resistant to pyrimethamine. Maintained by syringe passage under pyrimethamine pressure (100 mg/kg/i.p. x 1).

vi. ORA—derived from NK 65: Highly resistant to sulphonamides. Maintained by syringe passage under sulphaphenazole pressure (1000 mg/s.c x1)

vii Q—derived from N: Highly resistant to quinine, maintained by syringe passage under drug pressure (600 mg/kg quinine hydrochloride po x 1)

*P. yoelii* viii. *P. yoelii* nigeriensis (N67; NIG)—Maintained by syringe passage or cyclical transmission through *A. stephensi* (Beech strain) without drug pressure. Used as a model for chloroquine-sensitive *P. falciparum* for the causal prophylaxis studies.

ix *P. yoelii* ssp. NS—Moderately resistant to chloroquine. Maintained by cyclical passage through *Anopheles stephensi* and under drug pressure in mice (60 mg/kg s.c. x 1 at passage.).

x. MEF (=NS1100)—derived from NS: Highly resistant to mefloquine. Maintained by syringe passage under drug pressure (60 mg/kg s.c. x 1 at passage)

xi. SH—derived from NS: Highly resistant to halofantrine. Maintained by syringe passage under drug pressure (30 mg/kg s.c. x 1 at passage).

xii. ART—derived from NS: Highly resistant to artemisinin. Maintained by syringe passage under drug pressure (100 mg/kg s.c. x 1 at passage).

xiii SPN—derived from NS: Highly resistant to pyronaridine. Maintained by syringe passage under drug pressure (10 mg/kg sc x 1 at passage).

xiv. SAM—derived from NS: Highly resistant to amodiaquine Maintained by syringe passage under drug pressure (100 mg/kg sc x 1 at passage).

*P. vinckei petteri* xv. PET—Sensitive to all standard antimalarials. Syringe passaged, synchronous strain.

Protocols

Male, random-bred Swiss albino mice weighing 18–22 grams are inoculated intravenously with $10^7$ parasitised red blood cells of the above strains. Animals are then dosed once daily for four consecutive days beginning on the day of infection. Compounds are dissolved or suspended, using ultrasonication to achieve an even suspension, in sterile distilled water with Tween 80 and administered subcutaneously, intraperitioneally, orally or by such other route as may be required Where exceptional difficulty is encountered in preparing an aqueous preparation, the test compound is first dissolved in dimethyl sulfoxide and subsequently aqueous dilutions are prepared for use. The total amount of compound required is 250–1500 mg depending on active dose level found in preliminary screen. The parasitaemia is determined on the day following the last treatment and the $ED_{50}$ and $ED_{90}$ i.e. 50% and 90% suppression of parasites when compared with untreated controls, estimated from a plot of log dose against probit activity. Standard error is calculated with the aid of Table 48, Geigy Scientific Tables, 6th Edition. The degree of cross resistance is determined by comparing activity in the sensitive and resistant strains.

Drug Interaction Studies

The use of combinations of two or more compounds provides a means of protecting the individual components of the mixture from the development of resistance as well as being an efficient form of therapy, In addition, the potential exists for reversing drug-resistance by combining an appropriate compound with the antimalarial to which resistanced. New and better combinations might protect recently developed antimalarials from sharing the fate of most of the previous generation of drugs.

The "4-day test" technique has proved itself to be a sensitive system for detecting interactions between drugs. If two compounds are simultaneously administered in an appropriate series of dilutions then it is possible to determine the influence of one compound upon the $ED_{90}$ of the other in a series or ratios of combination. The $ED_{90}$ values obtained with combinations in a test of this type may be compared with those of the individual compounds to obtain an isobolar equivalent. These are plotted for each compound in an isobologram in order to demonstrate the presence of synergism, antagonism or a simple additive action.

The following results for the indicated pairs of Compounds A and B were obtained, and plotted to give the FIGS. 2 to 8.

Compound A: BO7  
$ED_{90}$: 4.2(1.6–11.0)  
Formulation: Distilled water/Tween 80  
Parasite: *P. berghei* Strain: N Compound B: Chloroquine  
$ED_{90}$: 3.0(1.4–8.0)

Figure 2:
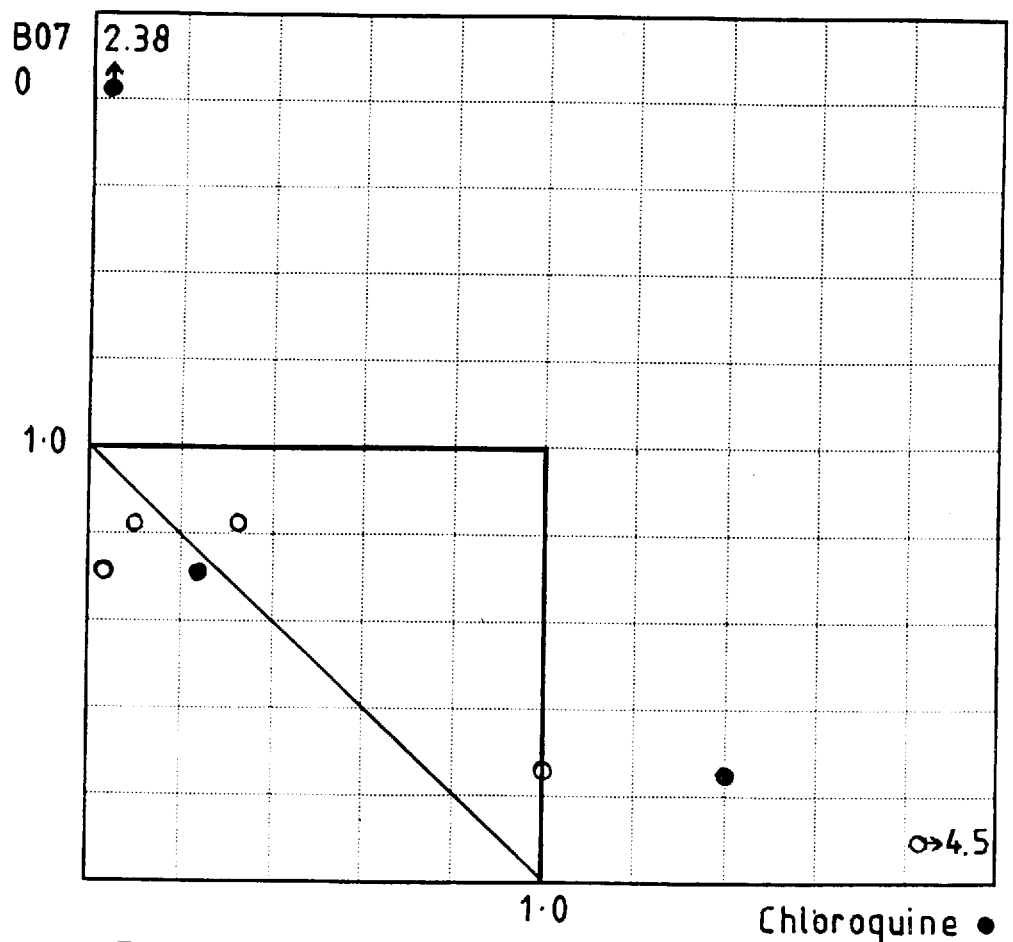
FIGS. 2 to 8 plot the test data for specific drug-drug combinations of this invention.

See FIG. 2

| Compound A +B (mg/kg) | mg/kg B as I.E. | $ED_{90}$ A | $ED_{90}$ A as I.E |
|---|---|---|---|
| 0.1 | 0.03 | 3.5 | 0.72 |
| 0.3 | 0.10 | 3.4 | 0.81 |
| 1.0 | 0.33 | 3.4 | 0.81 |
| 3.0 | 1.0 | 1.1 | 0.26 |

| Compound B +A (mg/kg) | mg/kg A as I.E. | $ED_{90}$ B | $ED_{90}$ B as I.E. |
|---|---|---|---|
| 0.3 | 0.07 | 13.5 | 4.5 |
| 1.0 | 0.24 | 4.2 | 1.4 |
| 3.0 | 0.71 | 0.7 | 0.23 |
| 10.0 | 2.38 | <0.1 | 0.03 |

Compound A: LON 2270 (BO7)  
$ED_{90}$: 5.4  
Formulation: distilled water/Tween 80  
Parasite: *P. yoelii* ssp Strain: NS Compound B: Chloroquine diphosphate  
$ED_{90}$: 28.0

Figure 3:
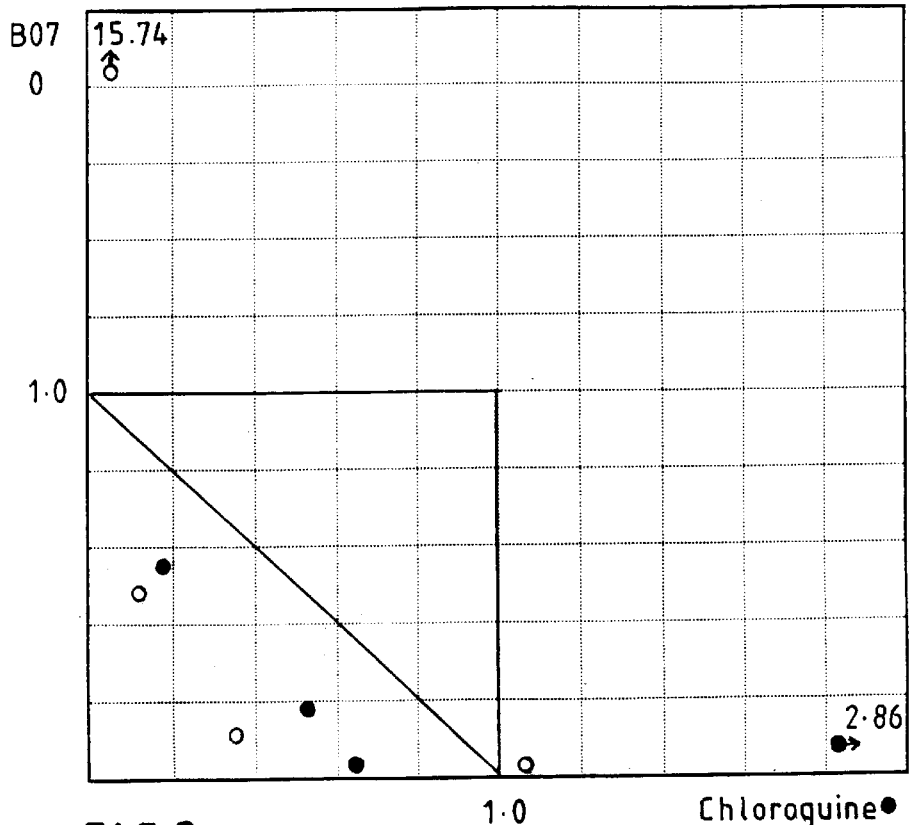

See FIG. 3

| Compound A +B (mg/kg) | mg/kg B as I.E. | $ED_{90}$ A | $ED_{90}$ A as I.E. |
|---|---|---|---|
| 1.0 | 0.04 | 85.0 | 15.74 |
| 3.0 | 0.11 | 2.5 | 0.46 |
| 10.0 | 0.36 | 0.6 | 0.11 |
| 30.0 | 1.07 | 0.4 | 0.07 |

-continued

| Compound B | +A (mg/kg) | mg/kg A as I.E. | $ED_{90}$ B | $ED_{90}$ B as I.E. |
|---|---|---|---|---|
| | 0.1 | 0.02 | 18.0 | 0.64 |
| | 0.3 | 0.06 | 80.0 | 2.86 |
| | 1.0 | 0.19 | 15.0 | 0.54 |
| | 30. | 0.56 | 4.6 | 0.16 |

Compound A: BO7  
$ED_{90}$: 1.4(0.8–1.7)  
Formulation: Distilled water/Tween 80  
Parasite: *P. berghei* Strain: N Compound B: Mefloquine HCl  
$ED_{90}$: 2.3(0.85–5.6)

Figure 4:
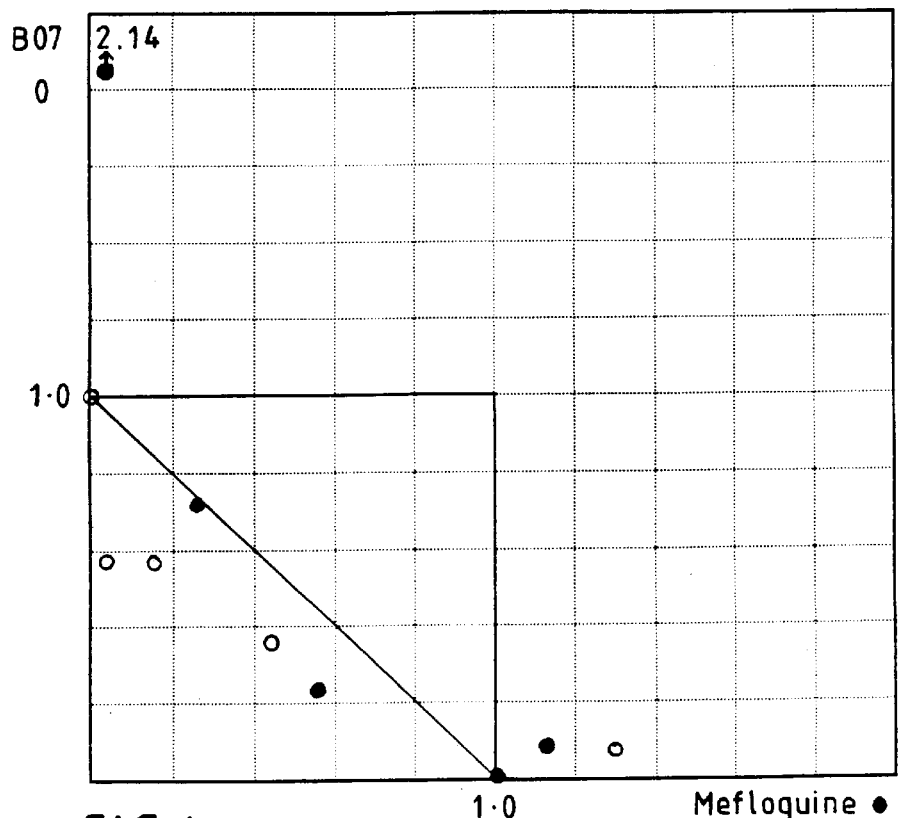

See FIG. 4

| Compound A | +B (mg/kg) | mg/kg B as I.E. | $ED_{90}$ A | $ED_{90}$ A as I.E. |
|---|---|---|---|---|
| | 0.1 | 0.04 | 0.8 | 0.57 |
| | 0.3 | 0.13 | 0.8 | 0.57 |
| | 1.0 | 0.43 | 0.5 | 0.36 |
| | 3.0 | 1.30 | 0.1 | 0.07 |

| Compound B | +A (mg/kg) | mg/kg A as I.E. | $ED_{90}$ B | $ED_{90}$ B as I.E. |
|---|---|---|---|---|
| | 0. | 0.07 | 2.6 | 1.13 |
| | 0.3 | 0.21 | 1.3 | 0.57 |
| | 1.0 | 0.71 | 0.57 | 0.25 |
| | 3.0 | 2.14 | <0.1 | 0.04 |

Compound A: BO7  
$ED_{90}$: 3.7(0.8–9.2)  
Formulation: Distilled water/Tween 80  
Parasite: *P. yoelii* ssp. Strain: NS Compound B: Mefloquine HCl  
$ED_{90}$: 6.0(3.6–9.8)

Figure 5:
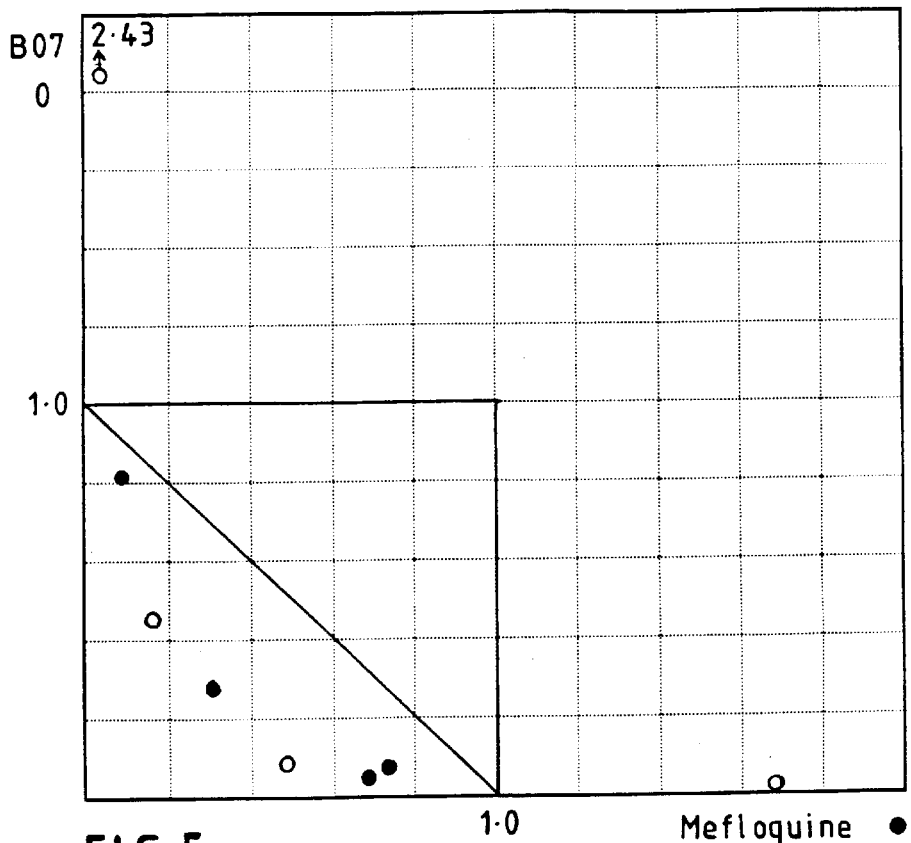

See FIG. 5

| Compound A | +B (mg/kg) | mg/kg B as I.E. | $ED_{90}$ A | $ED_{90}$ A as I.E. |
|---|---|---|---|---|
| | 0.3 | 0.05 | 9.0 | 2.43 |
| | 1.0 | 0.17 | 1.6 | 0.43 |
| | 3.0 | 0.50 | 0.4 | 0.07 |
| | 10.0 | 1.67 | 0.03 | 0.01 |

| Compound B | +A (mg/kg) | mg/kg A as I.E. | $ED_{90}$ B | $ED_{90}$ B as I.E. |
|---|---|---|---|---|
| | 0.1 | 0.03 | 4.1 | 0.68 |
| | 0.3 | 0.08 | 4.4 | 0.73 |
| | 1.0 | 0.27 | 1.9 | 0.31 |
| | 3.0 | 0.81 | 0.55 | 0.09 |

Compound A: LON 2270 (BO7)  
$ED_{90}$: 4.6  
Formulation: Distilled water/Tween 80  
Parasite: *P. berghei* Strain: N Compound B: Na Artesunate  
$ED_{90}$: 2.5

Figure 6:
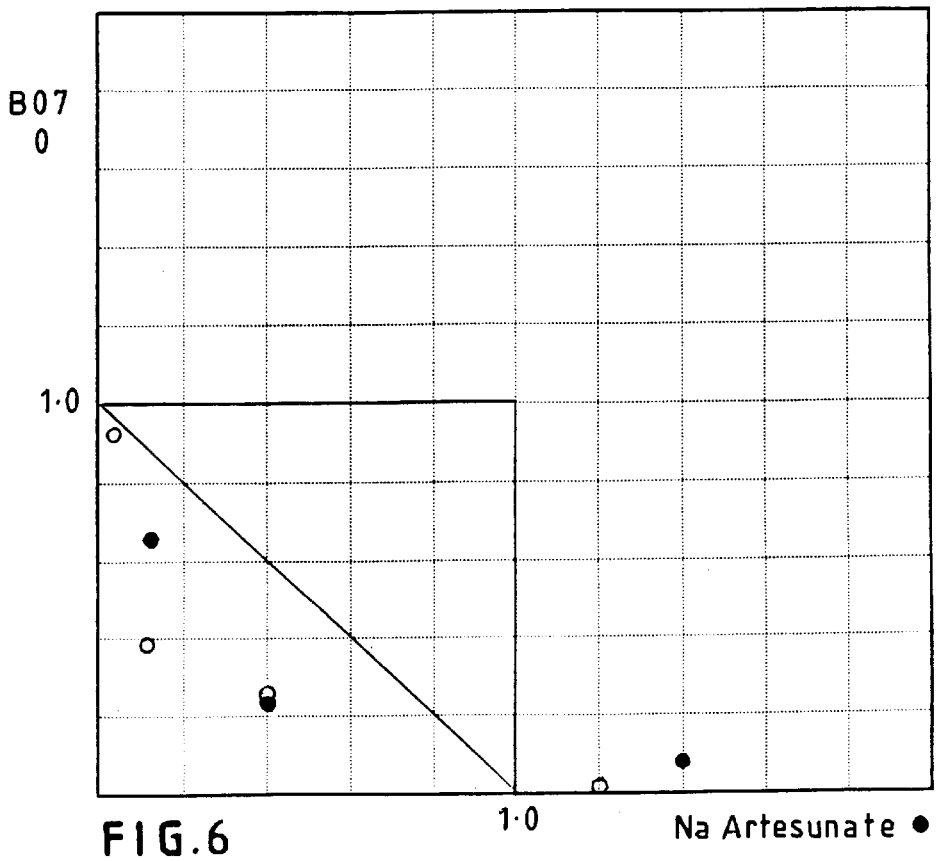

See FIG. 6

| Compound A | +B (mg/Kg) | mg/kg B as I.E. | $ED_{90}$ A | $ED_{50}$ A as I.E. |
|---|---|---|---|---|
| | 0.1 | 0.04 | 4.2 | 0.91 |
| | 0.3 | 0.12 | 1.8 | 0.39 |
| | 1.0 | 0.40 | 1.2 | 0.26 |
| | 3.0 | 1.20 | 0.2 | 0.04 |

| Compound B | +A (mg/kg) | mg/kg A as I.E. | $ED_{90}$ B | $ED_{90}$ B as I.E. |
|---|---|---|---|---|
| | 0.3 | 0.07 | 3.5 | 1.4 |
| | 1.0 | 0.22 | 1.0 | 0.4 |
| | 30. | 0.65 | 0.3 | 0.12 |
| | 10.0 | 2.17 | — | — |

Compound A: BO7  
$ED_{90}$: 4.8  
Formulation: Distilled water/Tween 80/DMSO  
Parasite: *P. vinckei* sp. Strain. *petteri*

Compound B: Na Artesunate  
$ED_{90}$: 1.0

Figure 7:
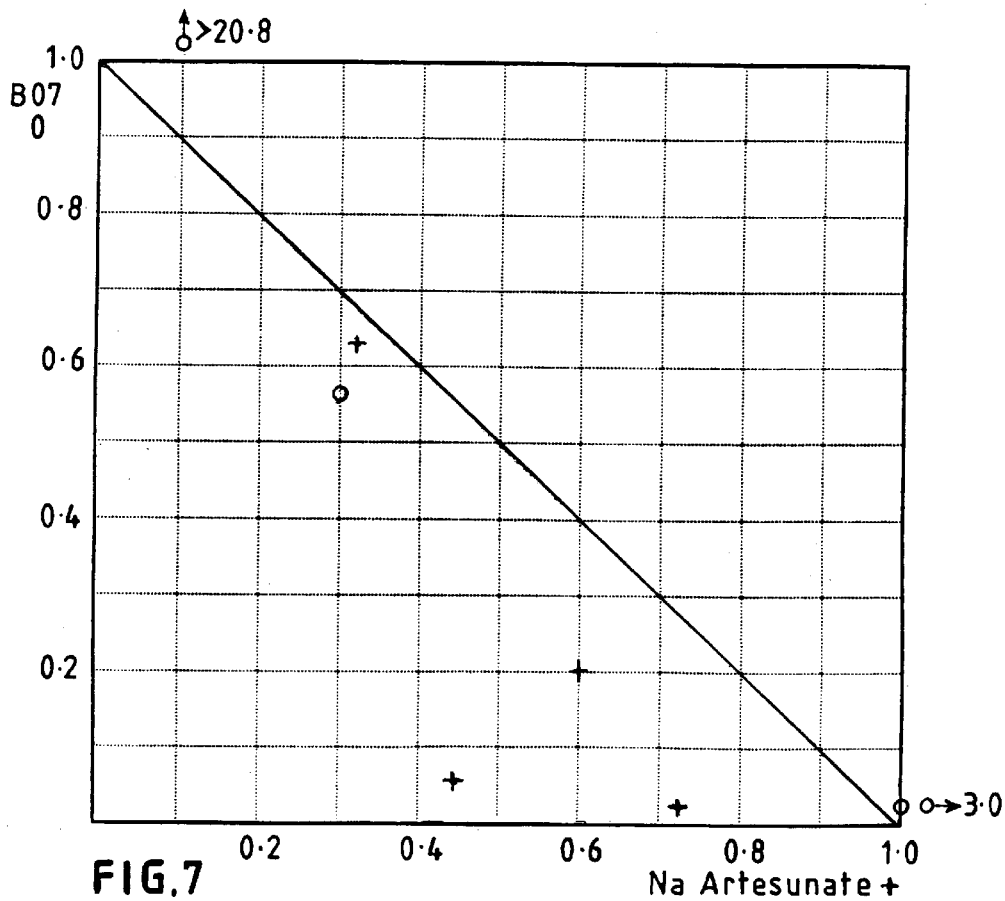

See FIG. 7

| Compound A | +B (mg/kg) | mg/kg B as I.E. | $ED_{90}$ A | $ED_{90}$ A as I.E. |
|---|---|---|---|---|
| | 0.1 | 0.1 | >100 | >20.8 |
| | 0.3 | 0.3 | 2.8 | 0.58 |
| | 1.0 | 1.0 | <0.1 | <0.02 |
| | 3.0 | 3.0 | <0.1 | 0.02 |

| Compound B | +A (mg/kg) | mg/kg A as I.E. | $ED_{90}$ B | $ED_{90}$ B as I.E. |
|---|---|---|---|---|
| | 0.1 | 0.02 | 0.72 | 0.72 |
| | 0.3 | 0.06 | 0.45 | 0.45 |
| | 1.0 | 0.2 | 0.6 | 0.6 |
| | 3.0 | 0.62 | 0.33 | 0.33 |

Compound A: LON 2270 (BO7)  
$ED_{90}$: 12.0  
Formulation: distilled water/Tween 80  
Parasite: *P. yoelii* ssp. Strain: ART Compound B: Artemisinin  
$ED_{90}$: 100

Figure 8:
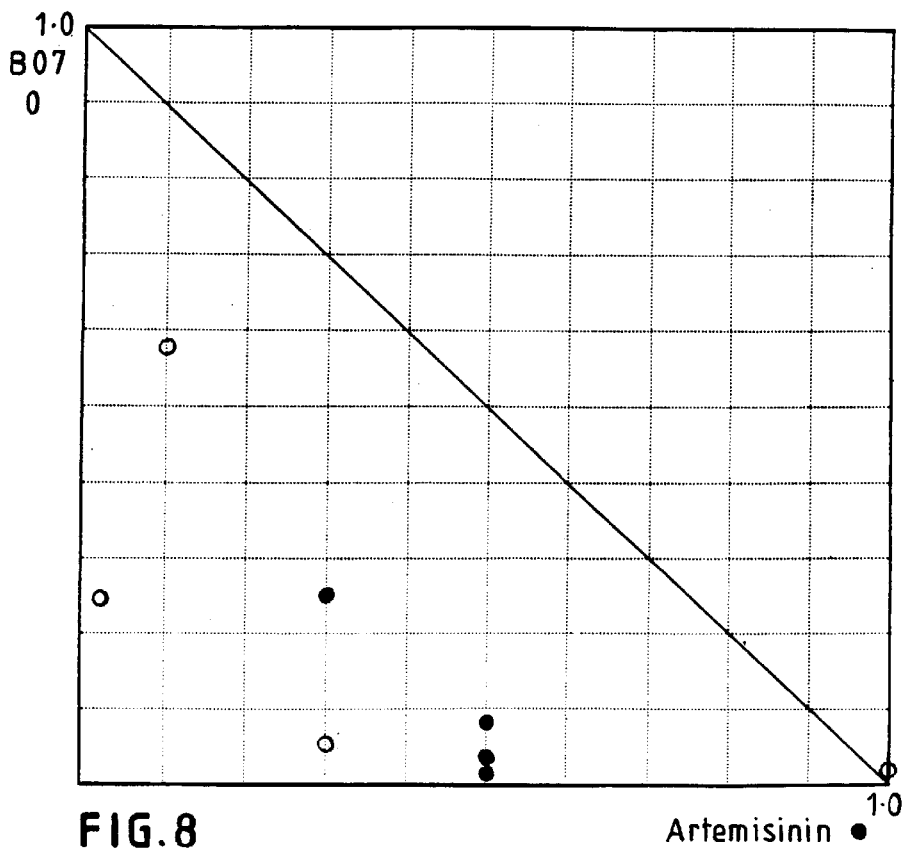

See FIG. 8

| Compound A | +B (mg/kg) | mg/kg B as I.E. | $ED_{90}$ A | $ED_{90}$ A as I.E. |
|---|---|---|---|---|
| | 3.0 | 0.03 | 3.0 | 0.25 |
| | 10.0 | 0.10 | 7.0 | 0.58 |
| | 30.0 | 0.30 | 0.6 | 0.05 |
| | 100.0 | 1.00 | 0.3 | 0.03 |

| Compound B | +A (mg/kg) | mg/kg A as I E. | $ED_{90}$ B | $ED_{90}$ B as I.E. |
|---|---|---|---|---|
| | 0.1 | 0.01 | 50.0 | 0.5 |
| | 0.3 | 0.03 | 50.0 | 0.5 |
| | 1.0 | 0.08 | 50.0 | 0.5 |
| | 3.0 | 0.25 | 30.0 | 0.3 |

Using isobolar equivalents of the observed $ED_{90}$ values, the data are plotted to indicate the possible presence of interaction in drug activities. When the data points fall approximately along the diagonal line, there is a simple additive effect. Points falling significantly below this line indicate a measure of synergism. Points grouping above the line indicate antagonism.

FIG. 2

With chloroquine and fenozan B07, there is an additive effect against *P. berghei* N, being a chloroquine sensitive strain.

FIG. 3

With chloroquine and fenozan B07, there is a synergistic effect against *P. yoelii* ssp NS, being a chloroquine resistant strain.

FIGS. 4 and 5

With mefloquine and fenozan B07, there is observed a clear-cut synergism.

FIGS. 6 and 7

The data for the interaction between sodium artesunate and fenozan B07 show a surprising degree of synergism.

FIG. 8

The data for the interaction between artemisinin and fenozan B07 show a surprising degree of synergism.

I claim:

1. An antimalarial drug combination useful for the prophylactic treatment or curative treatment of malaria, said combination comprising a first component which is a fenozan, that is a cis-fused cyclopenteno-1,2,3-trioxane, and a second component selected from the group consisting of artemisinin, sodium artesunate, chloroquine and mefloquine.

2. The drug combination of claim 1, wherein said first component is a cis-4a,7a-dihydro-7H-cyclopenta-1,2,4-trioxane.

3. The drug combination of claim 1, wherein said first component is a cis-4a,7a- dihydro-spiro(cyclopentane-3,3'-7H-cyclopenta-1,2,4-trioxane).

4. The drug combination of claim 1, wherein said first component is fenozan B07.

5. A pharmaceutical composition containing the drug combination of claim 1, together with a pharmaceutically acceptable carrier.

6. The pharmaceutical combination of claim 5, when formulated for oral administration.

7. A method of treating malaria comprising simultaneous or serial administration of an effective amount of an antimalarial drug combination, said combination comprising a first component which is a fenozan, that is a cis-fused cyclopenteno-1,2,4-trioxane, and a second component which is another antimalarial drug, selected from the group consisting of artemisinin, sodium artesunate, chloroquine and mefloquine.

* * * * *